United States Patent [19]

Costantini et al.

[11] Patent Number: 5,254,746
[45] Date of Patent: Oct. 19, 1993

[54] HYDROXYLATION OF PHENOLS/PHENOL ETHERS

[75] Inventors: Michel Costantini, Lyon; Jean-Michel Popa, Drancy; Michel Gubelmann, Lyon, all of France

[73] Assignee: Rhone-Poulenc Chimie, Courbevoie, France

[21] Appl. No.: 930,457

[22] Filed: Aug. 19, 1992

Related U.S. Application Data

[63] Continuation of Ser. No. 261,590, Oct. 24, 1988, abandoned.

[30] Foreign Application Priority Data

Oct. 29, 1987 [FR] France .................. 62-15247

[51] Int. Cl.⁵ .............................. C07C 43/11
[52] U.S. Cl. .................... 568/626; 568/629; 568/630; 568/771; 423/324; 423/325; 423/326; 502/242; 502/240; 502/232
[58] Field of Search ............... 568/629, 630, 771, 626; 502/64

[56] References Cited

U.S. PATENT DOCUMENTS 4,229,424  10/1980  Kokotailo .

FOREIGN PATENT DOCUMENTS 2024790  1/1980  United Kingdom .
2071071  9/1981  United Kingdom .
2116974  10/1983  United Kingdom .

OTHER PUBLICATIONS

*Chemical Reviews*, vol. 88, No. 1, p. 152, 1988.

*Primary Examiner*—José G. Dees
*Assistant Examiner*—Keith MacMillen
*Attorney, Agent, or Firm*—Burns, Doane, Swecker & Mathis

[57] ABSTRACT

The phenols and phenol ethers are hydroxylated by reaction with hydrogen peroxide in the presence of a catalytically effective amount of a titanozeosilite, advantageously a silicon oxide/titanium oxide MFI zeolite having the general formula:

$$Si_{(96-x)}, Ti_xO_{192}.$$

19 Claims, No Drawings

HYDROXYLATION OF PHENOLS/PHENOL ETHERS

This application is a continuation of application Ser. No. 07/261,590, filed Oct. 24, 1988, now abandoned.

CROSS-REFERENCE TO COMPANION APPLICATION

Our copending application Ser. No. 07/884,876, filed concurrently herewith and assigned to the assignee hereof.

BACKGROUND OF THE INVENTION

1. Field of the Invention

The present invention relates to the hydroxylation of phenols or phenol ethers with hydrogen and, more especially, to the hydroxylation of such phenols/phenol ethers with hydrogen peroxide in the presence of a catalytically effective amount of particular MFI zeolite.

2. Description of the Prior Art

The hydroxylation of phenol or substituted phenols with hydrogen peroxide, to prepare diphenols, is known to this art.

French Patent No. 69/45,467, published under No. 2,071,464, describes a process in which the reaction is catalyzed by a strong acid such as, for example, perchloric acid or sulfuric acid.

German Patent No. 2,410,742 describes a process similar to the above, in which hydrogen peroxide is employed in the form of a virtually anhydrous organic solution.

These two processes are quite attractive, and the first process is employed industrially.

However, over the past few years, an attempt has been made to catalyze the hydroxylation reaction using solids which are not dissolved in the reaction medium, in order to simplify their separation from such medium and their possible recycling, and to avoid the saline biproducts which most often are formed during the removal of the dissolved acid catalysts.

Thus, French Patent Application No. 81/17,023 (published under No. 2,489,816) recommends the use of titanium silicalite as a heterogeneous catalyst for the hydroxylation of aromatic compounds with hydrogen peroxide In fact, this catalyst presents extreme difficulties in respect of process reproducibility. In addition, the finely divided size of the catalyst particles makes their separation from the reaction medium very difficult and their recycling problematical whereas, in an industrial process, it is essential to be able to recycle an expensive catalyst.

To obviate this problem of separation of the catalyst, it has been proposed, in the European patent application published under No. 200,260, to use agglomerates of these fine particles of titanium silicalite.

Serious need continues to exist in this art, however, for a process for the heterogeneous catalysis of the hydroxylation of phenols or phenol ethers with hydrogen peroxide which can be carried out on an industrial scale under economically acceptable conditions.

SUMMARY OF THE INVENTION

Accordingly, a major object of the present invention is the provision of an improved process for the hydroxylation of phenols/phenol ethers which is well adopted to be carried out on an industrial scale.

Briefly, the present invention features the hydroxylation of phenols or phenol ethers having the general formula (I):

in which $R_5$ is a hydrogen atom a methyl group, an ethyl group or a phenyl group, and $R_6$ is a hydrogen atom, an alkyl radical having from 1 to 4 carbon atoms, an alkoxy radical having from 1 to 4 carbon atoms or a phenyl or cyclohexyl radical, comprising reacting such phenols/phenol ethers with hydrogen peroxide in the presence of a catalytically effective amount of a zeolite of MFI structure based on silicon oxide and titanium oxide, and having the following formula (II) after calcination thereof:

$$Si_{96-x}, Ti_xO_{192} \quad (II)$$

in which x ranges from about 0.1 to about 6.

DETAILED DESCRIPTION OF THE PREFERRED EMBODIMENTS OF THE INVENTION

More particularly according to the present invention, the subject zeolites will hereinafter be designated as titanozeosilites.

The titanozeosilites employed in the process of the invention have a monoclinic crystalline system and an X-ray diffraction pattern as set forth in Table I.

In this table, the extreme values of the different interplanar spacings $d_{hkl}$ are given and correspond to the limiting concentrations of titanium incorporated in the zeolite lattice, or more precisely to the Ti/Si ratio.

In effect, the identification of titanozeosilites may, in particular, be advantageously carried out by establishing their X-ray diffraction pattern.

TABLE I

| X-ray diffraction pattern | | | |
|---|---|---|---|
| Extreme values of $d_{hkl}$ (nm) | $I/I_o$ | Extreme values of $d_{hkl}$ (nm) | $I/I_o$ |
| 1.110–1.128 | S–SS | 0.3785–0.3845 | mS |
| 0.991–1.012 | S–SS | 0.3735–0.3795 | m |
| 0.972–0.986 | w | 0.3715–0.3775 | m |
| 0.895–0.906 | ww | 0.3705–0.3765 | m |
| 0.803–0.813 | ww | 0.3645–0.3700 | w |
| 0.741–0.753 | ww (broad) | 0.3610–0.3670 | w |
| 0.704–0.715 | ww (broad) | 0.3470–0.3525 | ww |
| 0.666–0.678 | w | 0.3430–0.3485 | w (w) |
| 0.632–0.643 | w | 0.3415–0.3470 | w (w) |
| 0.595–0.605 | mw | 0.3385–0.3439 | ww |
| 0.589–0.598 | w | 0.3341–0.3394 | w (w) |
| 0.568–0.577 | mw | 0.3290–0.3345 | w (broad) |
| 0.565–0.574 | w (shoulder) | 0.3240–0.3292 | w |
| 0.555–0.564 | w | 0.3045–0.3099 | w (w) |
| 0.534–0.543 | w (w) | 0.3020–0.3068 | w |
| 0.531–0.539 | w (w) | 0.2978–0.3026 | w |
| 0.510–0.518 | ww | 0.2952–0.2999 | ww (shoulder) |
| 0.502–0.508 | ww | 0.2944–0.2991 | w |
| 0.496–0.504 | mw | 0.2914–0.2961 | ww |
| 0.485–0.493 | ww | 0.2852–0.2898 | ww (broad) |
| 0.468–0.476 | ww | 0.2774–0.2818 | ww |
| 0.459–0.466 | w | 0.2722–0.2766 | ww (broad) |
| 0.444–0.451 | w | 0.2676–0.2720 | ww |
| 0.433–0.441 | w | 0.2606–0.2648 | ww |
| 0.423–0.431 | w | 0.2586–0.2627 | ww |
| 0.4055–0.4125 | ww | 0.2544–0.2585 | ww (broad) |
| 0.3985–0.4045 | w | 0.2508–0.2548 | ww |

TABLE I-continued

| Extreme values of $d_{hkl}$ (nm) | X-ray diffraction pattern | | |
|---|---|---|---|
| | $I/I_o$ | Extreme values of $d_{hkl}$ (nm) | $I/I_o$ |
| 0.3835–0.3905 | S | 0.2478–0.2518 | w |
| 0.3805–0.3865 | mS | | |

The above diffraction pattern may be obtained using a diffractometer, employing the classical powder method with the Kα radiation of copper. From the position of the diffraction peaks represented by the angle 2Θ, the interplanar spacings $d_{hkl}$ characteristics of the sample are calculated by the Bragg equation. The estimate of the error of measurement, $(d_{hkl})$ over $d_{hkl}$, is calculated, in terms of the absolute error (2Θ) assigned to the measurement of 2Θ, by the Bragg equation. An absolute error (2Θ) equal to $\pm 0.2°$ is commonly accepted. The relative intensity $I/I_o$ assigned to each value of $d_{hkl}$ is estimated from the height of the corresponding diffraction peak. A scale of symbols is often used for characterizing this intensity: SS=very strong, S=strong, mS=moderate to strong, m=moderate, mw=moderate to weak, w=weak, ww=very weak.

In general, titanozeosilite contains fluorine; the fluorine concentration advantageously ranges from 0.01 to 0.8% by weight after calcination.

However, the fluorine can be removed without thereby modifying the structure of the titanozeosilite according to the invention.

The titanozeosilite used as the catalyst in the process of the invention may be synthesized in the following manner:

(i) first preparing a reaction mixture, in an aqueous medium, containing at least one source of silicon oxide, one source of titanium oxide, fluoride ions and a structuring agent, the pH of such reaction mixture ranging from approximately 1.5 to approximately 10.5;

(ii) next crystallizing this reaction mixture and recovering the crystalline precipitate therefrom; and (iii) calcining such precipitate at a temperature above 450° C.

The X-ray diffraction pattern set forth in Table I is that of a titanozeosilite subjected to a calcination as described above.

The presence of fluoride ions in the reaction medium, which serve the function of a mobilizing agent, enable a solubilization of the T species (Si and Ti) to be obtained in a medium having a pH of less than 10. Thus, it is possible to use $NH_4^{30}$ ions as compensating cations, which may be completely removed, if so desired, during the calcination.

In addition, since the crystallization is carried out in a medium having a pH of less than 10, the rate of nucleation is slower. Thus, it is possible to obtain crystals of titanozeosilites controlled by directing the rate of nucleation.

The mole ratios between the different species in the reaction medium range, for Ti/Si, from approximately 1.5 to approximately 0.002, for F/Si from 10 to approximately 0.04, for $H_2O$/Si from approximately 400 to approximately 4, and, for the structuring agent relative to the silicon species, from approximately 2 to approximately 0.02.

Advantageously, the mole ratio Ti/Si ranges from 1 to 0.01, F/Si from 6 to 0.06, $H_2O$/Si from 100 to 6, and, between the structuring agent and the silicon species, from 1 to 0.04.

Many sources of silica may be used. By way of example, representative are the silicas in the form of hydrogels, aerogels and colloidal suspensions, silicas resulting from precipitation from solutions of soluble silicates or from the hydrolysis of silicic esters such as $Si(OC_2H_5)_4$ or of complexes such as $Na_2SiF_6$, and silicas prepared by extraction and activation treatments of natural or synthetic crystallized compounds such as aluminum silicates, aluminosilicates and clays. It is also possible to use hydrolyzable compounds of tetravalent silicon such as silicon halides.

Among the sources of titanium oxide, exemplary are crystallized or amorphous titanium oxides and hydroxides, tetravalent titanium compounds capable of being hydrolyzed such as the halides ($TiCl_4$), alcoholates, and soluble titanium salts such as $TiOSO_4$ and $(NH_4)_2TiO(C_2O_4)_2$.

It is also possible to use, as sources of the silica or of the titanium oxide, compounds comprising the elements Si and Ti such as, for example, glasses or gels based on the oxides of these two elements.

The sources of silica and of titanium oxide may be introduced in soluble form or in the form of pulverulent solids, but also in the form of agglomerates such as, for example, pellets or extrudates capable of being converted to a titanozeosilite of the desired structure without a modification in form.

The fluoride anions may be introduced in the form of hydrofluoric acid, of salts such as, for example, $NH_4F$, $NH_4HF_2$, $NH(C_3H_7)_3F$, $N(C_3H_7)_4F$, or of hydrolyzable compounds liberating fluoride anions into the reaction medium, such as, for example, $SiF_4$, $(NH_4)_2SiF_6$, $(NH_4)_2TiF_6$ or the like.

Ammonium fluoride or ammonium bifluoride are the preferred salts. In effect, these salts are very soluble and contribute no undesirable element and they are, in addition, easily removed upon completion of the crystallization.

The structuring agents suitable for the preparation of the titanozeosilites are:

(i) the amines of the formula (III):

in which $R_1$, $R_2$ and $R_3$, which may be identical or different, are each an alkyl group, preferably a propyl or butyl group;

(ii) the quaternary ammonium compounds of the formula (IV):

in which $R_1$, $R_2$, $R_3$ and $R_4$, which may be identical or different, are each an alkyl group, preferably a propyl or butyl group; and (iii) the compounds of formulae (III) and (IV) in which the nitrogen has been replaced by a phosphorus atom.

The structuring agents are preferably tripropylamine or compounds capable of yielding tetrapropylammonium cations.

Advantageously, the structuring agent is added to the reaction mixture in the form of an amine salt or a quaternary ammonium salt yielding the abovementioned cations.

The reaction mixture can comprise a co-mobilizing agent for the tetravalent titanium, in a mole ratio relative to the silicon of from 3 to 0.01 and advantageously from 2 to 0.4.

The co-mobilizing agents which are suitable for the preparation of the titanozeosilites used in the present process are, for example, oxalic acid and its salts and tartaric acid and its salts.

The crystallization of the titanozeosilite may be effected by heating the reaction mixture to a temperature of from approximately 50° C. to approximately 240° C., and preferably from 75° C. to 225° C., for the time required for crystallization, according to the traditional procedure for the synthesis of zeolites well known to this art. For example, the heating time may range from approximately 6 hours to 500 hours.

This heating and crystallization are preferably carried out in a vessel or autoclave coated with a layer such as, for example, of polytetrafluoroethane.

The reaction may be stirred or otherwise.

After crystallization, the resulting precipitate is recovered, for example, by filtration.

This precipitate is then heated after an optional drying, to a temperature above 450° C., and preferably above 500° C., in order to decompose, by calcination or thermal decomposition, the organic species present in the precipitate, such as, for example, the structuring agent, and the compensating cations ($NH_4^{30}$).

The phenols and phenol ethers which are preferably hydroxylated in the process of the invention are the compounds of formula (I) in which $R_5$ is a hydrogen atom, a methyl group or an ethyl group, and $R_6$ is a hydrogen atom, a methyl, ethyl or tert-butyl group or a methoxy or ethoxy group.

Exemplary are phenol, anisole, ortho-cresol, meta-cresol, para-cresol, 4-tert-butylphenol, 2-methoxyphenol and 4-methoxyphenol.

The process according to the invention is especially applicable to phenol for the preparation of hydroquinone and pyrocatechol.

The hydrogen peroxide may be used in the form of an aqueous solution generally having a hydrogen peroxide concentration greater than 20% by weight. The hydrogen peroxide may also be used in the form of a solution in an organic solvent. Exemplary organic solvents which are useful for the introduction of the hydrogen peroxide are esters such as, in particular, alkyl or cycloalkyl esters of saturated aliphatic carboxylic acids; preferably, alkyl acetates and propionates having a total of 4 to 8 carbon atoms, or mixtures of such esters, will be employed. It is also possible to use solutions of hydrogen peroxide in an ether such as, for example, dioxane, diisopropyl ether or methyl tert-butyl ether.

The mole ratio compound of formula I/hydrogen peroxide generally ranges from 25:1 to 3:1, and preferably from 20:1 to 4:1.

The amount of titanozeosilite, defined above, which can be employed in the present process can vary over very wide limits.

When the process is carried out in discontinuous fashion, the catalyst can constitute from 0.1% to 20% by weight relative to the weight of the compound of formula (I) introduced. Preferably, this weight ratio ranges from 0.5% to 10%. However, if the process is carried out in continuous fashion, for example by reacting a mixture of compound (I) and hydrogen peroxide solution on a fixed bed of catalyst, these catalyst/compound (I) ratios are no longer meaningful and, at any given instant, it is possible to have a weight excess of catalyst relative to the compound (I).

It is also possible to carry out the hydroxylation reaction of the compound (I) in a solvent for the compound (I), which is preferably miscible or partially miscible with water.

Exemplary of such solvents are water; alcohols such as methanol, tert-butanol, isopropanol or ethanol; ketones such as acetone or methyl isobutyl ketone; nitriles such as acetonitrile; carboxylic acids such as acetic acid; esters such as propyl acetate; ethers such as methyl tert-butyl ether; and polar aprotic solvents such as tetrahydrothiophene dioxide (sulfolane), ethylene glycol carbonate, propylene glycolcarbonate or N-methylpyrrolidone.

The temperature at which the reaction is carried out generally ranges from 45° C. to 160° C. under atmospheric pressure. It is also possible to carry out the reaction at a higher temperature and under a pressure above atmospheric pressure.

In order to further illustrate the present invention and the advantages thereof, the following specific examples are given, it being understood that same are intended only as illustrative and in nowise limitative.

EXAMPLE 1

Preparation of the Catalysts (1a) and (1b)

Catalyst (1a)

A reaction mixture was prepared according to the following procedure:

5.45 g of $Ti(OC_4H_9)_4$ were hydrolyzed in 100 cm$^3$ of water by stirring this mixture for 6 hours. The resulting precipitate was filtered off and then dissolved in the heated state in 107 cm$^3$ of water, in the presence of 4.03 g of oxalic acid ($C_2H_2O_4.2\ H_2O$). To this solution of titanium oxalate, a solution containing 10.65 g of tetrapropylammonium bromide (TPA-Br), 2.96 g of ammonium fluoride ($NH_4F$), 0.19 g of zeolite MFI seeds and 9.6 g of Aerosil 130 type silica was added.

The mixture was stirred for approximately 15 minutes.

The molar composition, referred to one mole of silica, of the reaction mixture was as follows: 1 $SiO_2$; 0.1 $TiO_2$; 0.2$C_2H_2O_4$; 0.25 TPA-Br; 0.5 $NH_4F$; 37 $H_2O$.

The reaction mixture was then crystallized in an autoclave coated internally with PTFE, by heating to 170° C. for 7 days without stirring.

After crystallization, the solid phase was separated off by filtration, washed with water and dried at 80° C. After calcination at 550° C. for 4 hours, the solid phase was identified by its X-ray diffraction pattern. It was found to contain more than 90% of titanozeosilite.

The titanozeosilite was in the form of long, fine crystals (with small beads) measuring 15 to 20 micrometers.

Chemical analysis performed on the product of Example (1a) evidenced an overall mole ratio Si/Ti of 25. The estimate of the mole ratio Si/Ti in the zeolite lattice may be made on the basis of the measurement of the relative shifts of the diffraction peaks. A value equal to approximately 60 was then found.

The X-ray diffraction pattern of the titanozeosilite produced in Example (1a) is set forth below.

| $d_{hkl}$ (nm) | $I/I_o$ |
| --- | --- |
| 0.462 | w |
| 0.446 | ww |
| 0.436 | w |
| 0.426 | w |
| 0.4084 | ww |
| 0.4008 | w |
| 0.3859 | S |
| 0.3826 | mS |
| 0.3806 | mS |
| 0.3759 | m |
| 0.3742 | m |
| 0.3718 | m |
| 0.3663 | w |
| 0.3627 | w |
| 0.3448 | w(w) |
| 0.3431 | w |
| 0.3396 | ww |
| 0.3357 | w(w) |
| 0.3317 | w |
| 0.3256 | w |

Catalyst (1b)

A reaction mixture was prepared according to the following procedure:

2.72 g of $Ti(OC_4H_9)_4$ were hydrolyzed in 50 cm$^3$ of water by stirring this mixture for 6 hours. The resulting precipitate was filtered off and then dissolved in the heated state in 4.32 cm$^3$ of water, in the presence of 2.02 g of oxalic acid ($C_2H_2O_4.2\ H_2O$). To this solution of titanium oxalate, a solution containing 5.33 g of tetrapropylammonium bromide (TPA-Br), 1.48 g of ammonium fluoride ($NH_4F$), 0.096 g of zeolite MFI seeds and 4.8 g of Aerosil 130 type silica was added.

The mixture was stirred for approximately 15 minutes.

The molar composition, referred to one mole of silica, of the reaction mixture was as follows: 1 $SiO_2$; 0.1 $TiO_2$; 0.2 $C_2H_2O_4$; 0.25 TPA-Br; 0.5 $NH_4F$; 30 $H_2O$.

The relative mixture was then crystallized in an autoclave coated internally with PTFE, by heating to 200° C. for 6 days without stirring.

After crystallization, the solid phase was separated off by filtration, washed with water and dried at 70° C. After calcination at 550° C. for 4 hours, the solid phase was identified by its X-ray diffraction pattern. It was found to contain more than 90% of titanozeosilite.

The titanozeosilite was in the form of very fine, elongated crystals approximately 10 micrometers in length.

Chemical analysis performed on the product of Example (1b) evidenced an overall mole ratio Si/Ti of 25. The estimate of the mole ratio Si/Ti in the zeolite lattice may be made on the basis of the measurement of the relative shifts of the diffraction peaks. A value equal to approximately 60 was then found.

The X-ray diffraction pattern of the titanozeosilite produced in Example (1b) was the same as in Example (1a).

EXAMPLE 2

A 100-cm$^3$ pyrex glass reactor equipped with a central stirrer, a condenser linked to a gas holder, a regulated heating system and an injection system was charged with the following materials after the apparatus had been purged beforehand with nitrogen:

(i) 26.95 g of phenol;

(ii) 0.513 g of titanozeosilite prepared in Example (1a).

The mixture was heated to 80° C. under stirring, and a 40% strength (weight/volume) aqueous solution of $H_2O_2$ (0.063 mol of $H_2O_2$) was then injected therein.

The mixture was then permitted to react for an additional 2 hours.

After the catalyst was filtered off, unconverted $H_2O_2$ was assayed by iodometry, and the diphenols by high performance liquid chromatography (HPLC).

The following results were obtained:
(a) Degree of conversion (DC) of $H_2O_2$: 24.1%
(b) Yield of pyrocatechol relative to $H_2O_2$ converted (YLD): 16.0%
(c) Yield of hydroquinone relative to $H_2O_2$ converted (YLD): 25.0%
(d) Total yield of diphenols: 41.0%

EXAMPLE 3

A 30-cm$^3$ pyrex glass reactor equipped with central stirring by a bar magnet, a condenser linked to a gas holder, a regulated heating system and an injection system was charged with the following materials after the apparatus had been purged beforehand with nitrogen:

(i) 9.4 g of phenol (0.1 mol); (ii) 0.25 g of titanozeosilite prepared in Example (1a).

The mixture was heated to 80° C. under stirring, and a 70% strength (weight/volume) aqueous solution of $H_2O_2$ (0.005 mol of $H_2O_2$) was then injected therein.

The mixture was then permitted to react for 2 hours, 30 minutes

After the catalyst was filtered off, unconverted $H_2O_2$ was assayed by iodometry, and the diphenols by high performance liquid chromatography (HPLC).

The following results were obtained:
(a) Degree of conversion (DC) of $H_2O_2$: 30.5%
(b) Yield of pyrocatechol relative to $H_2O_2$ converted (YLD): 24.0%
(c) Yield of hydroquinone relative to $H_2O_2$ converted (YLD): 36.0%
(d) Total yield of diphenols: 60.0%

EXAMPLE 4

Example 3 was repeated with the same amounts of reactants, but the experiment was carried out at 130° C. instead of 80° C.

The following results were obtained:
(a) Degree of conversion (DC) of $H_2O_2$: 93.0%
(b) Yield of pyrocatechol relative to $H_2O_2$ converted (YLD): 35.5%
(c) Yield of hydroquinone relative to $H_2O_2$ converted (YLD): 33.0%
(d) Total yield of diphenols: 68.5%

EXAMPLES 5 TO 11

A 30-cm$^3$ pyrex glass reactor equipped with a magnetic stirrer, a condenser linked to a gas holder, a regulated heating system and an injection system was charged with the following materials after the apparatus had been purged beforehand with nitrogen:

(i) 4.7 g of phenol;
(ii) 0.25 g of titanozeosilite prepared in Example 1 ((1a) for Examples 5 to 9, (1b) for Examples 10 to 11);
(iii) 4.7 g of a solvent (see Table II below).

The mixture was heated to 80° C. under stirring, and a 70% strength (weight/volume) solution of $H_2O_2$ (2.5 mmol) was then injected therein.

The mixture was then permitted to react for 2 h, 30 min.

After the catalyst was filtered off, unconverted $H_2O_2$ was assayed by iodometry, and the diphenols by high performance liquid chromatography (HPLC).

The Table II below reports the results obtained (pyrocatechol=PC; hydroquinone=HQ).

TABLE II

| EXAMPLE | SOLVENT | DC % $H_2O_2$ | YLD % HQ | YLD % PC | Sum YLD % |
|---|---|---|---|---|---|
| 5 | acetic acid | 70.0 | 11.0 | 8.5 | 19.5 |
| 6 | acetonitrile | 7.5 | 30.0 | 60.0 | 90.0 |
| 7 | methyl iso-butyl ketone | 14.0 | 13.0 | 17.5 | 30.5 |
| 8 | tert-butanol | 6.0 | 42.0 | 52.5 | 94.5 |
| 9 | sulfolane | 28.0 | 16.0 | 20.0 | 36.0 |
| 10 | water | 73.0 | 26.0 | 51.0 | 77.0 |
| 11 | methyl tert-butyl ether | 2.5 | 48.0 | 48.0 | 96.0 |

EXAMPLE 12

Example 10 was repeated according to the procedure described for Examples 5 to 11, but operating at 100° C., (with water as solvent).

The experimental treatment and the assays were carried out as in Examples 5 to 11.

The following results were obtained:

(a) Degree of conversion of $H_2O_2$: 92.5%

(b) Yield of pyrocatechol relative to $H_2O_2$ converted: 39.0%

(c) Yield of hydroquinone relative to $H_2O_2$ converted: 39.5%

(d) Yield of diphenols relative to $H_2O_2$ converted: 78.5%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydroxylation of a phenol or phenol ether having the general formula (I):

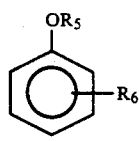

in which $R_5$ is a hydrogen atom, a methyl group, an ethyl group or a phenyl group, and $R_6$ is a hydrogen atom, an alkyl radical having from 1 to 4 carbon atoms, an alkoxy radical having from 1 to 4 carbon atoms or a phenyl or cyclohexyl radical, comprising reacting such phenol or phenol ether with hydrogen peroxide in the presence of a catalytically effective amount of a titanozeosilite comprising an MFI zeolite based on titanium oxide and silicon oxide and having a monoclinic crystalline structure.

2. The process as defined by claim 1, said titanozeosilite comprising an MFI zeolite based on silicon oxide and titanium oxide and having, after calcination, the following formula (II):

$$Si_{(96-x)}Ti_xO_{192} \quad (II)$$

in which x ranges from about 0.1 to 6.

3. The process as defined by claim 2, said titanozeosilite further comprising from 0.01 to 0.8% of fluorine by weight, after calcination.

4. The process as defined by claim 2, wherein formula (I), $R_5$ is a hydrogen atom, a methyl group or an ethyl group, and $R_6$ is a hydrogen atom, a methyl, ethyl or tert-butyl group, or a methoxy or ethoxy group.

5. The process as defined by claim 2, said phenol or phenol ether having the formula (I) comprising phenol, anisole, ortho-cresol, meta-cresol, para-cresol, 4-tert-butylphenol, 2-methoxyphenol or 4-methoxyphenol.

6. The process as defined by claim 1, wherein the mole ratio phenol/phenol ether to hydrogen peroxide ranges from 25:1 to 3:1.

7. The process as defined by claim 1, carried out discontinuously, and wherein the catalyst constitutes from 0.1% to 20% by weight of the weight of the compound of formula (I).

8. The process as defined by claim 1, carried out continuously on a fixed bed of catalyst.

9. The process as defined by claim 2, said titanozeosilite having been produced by:

(i) first preparing a reaction mixture, in an aqueous medium, containing at least one source of silicon oxide, one source of titanium oxide, fluoride ions and a structuring agent, the pH of such reaction mixture ranging from approximately 1.5 to approximately 10.5;

(ii) crystallizing such reaction mixture and recovering the crystalline precipitate therefrom; and (iii) calcining such precipitate at a temperature above 450° C.

10. The process as defined by claim 9, wherein, during the preparation of the titanozeosilite, the mole ratio Ti/Si in the reaction mixture ranges from 1 to 0.01.

11. The process as defined by claim 9, wherein, during the preparation of the titanozeosilite, the mole ratio F/Si in the reaction mixture ranges from 6 to 0.06.

12. The process as defined by claim 9, wherein, during the preparation of the titanozeosilite, the mole ratio $H_2O$/Si in the reaction mixture ranges from 100 to 6.

13. The process as defined by claim 9, wherein, during the preparation of the titanozeosilite, the mole ratio structural agent/Si ranges from 1 to 0.04.

14. The process as defined by claim 1, said hydrogen peroxide comprising an aqueous solution thereof.

15. The process as defined by claim 1, said hydrogen peroxide comprising an organic solution thereof.

16. The process as defined by claim 1, carried out in a solvent for the compound of formula (I).

17. The process as defined by claim 16, said solvent comprising water, an alcohol, a ketone, a nitrile, a carboxylic acid, an ester, an ether, or a polar aprotic solvent.

18. The process as defined by claim 1, carried out at a temperature of from 45° C. to 160° C.

19. The process as defined by claim 1, said titanozeosilite having the x-ray diffraction pattern comprising:

| Extreme values of $d_{hkl}$ (nm) | $I/I_0$ | Extreme values of $d_{hkl}$ (nm) | $I/I_0$ |
|---|---|---|---|
| 1.110–1.128 | S-SS | 0.3785–0.3845 | mS |
| 0.991–1.012 | S-SS | 0.3735–0.3795 | m |

-continued

| Extreme values of $d_{hkl}$ (nm) | $I/I_o$ | Extreme values of $d_{hkl}$ (nm) | $I/I_o$ |
|---|---|---|---|
| 0.972–0.986 | w | 0.3715–0.3775 | m |
| 0.895–0.906 | ww | 0.3705–0.3765 | m |
| 0.803–0.813 | ww | 0.3645–0.3700 | w |
| 0.741–0.753 | ww (broad) | 0.3610–0.3670 | w |
| 0.704–0.715 | ww (broad) | 0.3470–0.3525 | ww |
| 0.666–0.678 | w | 0.3430–0.3485 | w (w) |
| 0.632–0.643 | w | 0.3415–0.3470 | w (w) |
| 0.595–0.605 | mw | 0.3385–0.3439 | ww |
| 0.589–0.598 | w | 0.3341–0.3394 | w (w) |
| 0.568–0.577 | mw | 0.3290–0.3345 | w (broad) |
| 0.565–0.574 | w (shoulder) | 0.3240–0.3292 | w |
| 0.555–0.564 | w | 0.3045–0.3099 | w (w) |

-continued

| Extreme values of $d_{hkl}$ (nm) | $I/I_o$ | Extreme values of $d_{hkl}$ (nm) | $I/I_o$ |
|---|---|---|---|
| 0.534–0.543 | w (w) | 0.3020–0.3068 | w |
| 0.531–0.539 | w (w) | 0.2978–0.3025 | w |
| 0.510–0.518 | ww | 0.2952–0.2999 | ww (shoulder) |
| 0.502–0.508 | ww | 0.2944–0.2991 | w |
| 0.496–0.504 | mw | 0.2914–0.2961 | ww |
| 0.485–0.493 | ww | 0.2852–0.2898 | ww (broad) |
| 0.468–0.476 | ww | 0.2774–0.2818 | ww |
| 0.459–0.466 | w | 0.2722–0.2766 | ww (broad) |
| 0.444–0.451 | w | 0.2676–0.2720 | ww |
| 0.433–0.441 | w | 0.2606–0.2648 | ww |
| 0.423–0.431 | w | 0.2586–0.2627 | ww |
| 0.4055–0.4125 | ww | 0.2544–0.2585 | ww (broad) |
| 0.3985–0.4045 | w | 0.2508–0.2548 | ww |
| 0.3835–0.3905 | S | 0.2478–0.2518 | w |
| 0.3805–0.3865 | mS. | | |

* * * * *